United States Patent [19]

Habashi et al.

[11] Patent Number: 5,277,176
[45] Date of Patent: Jan. 11, 1994

[54] EXTRACORPOREAL LUNG ASSISTANCE APPARATUS AND PROCESS

[76] Inventors: Nader M. Habashi, 224 S. Caswell Rd., Charlotte, N.C. 28204; Howard N. Reynolds, 12 Severn River Rd., Severna Park, Md. 21146; Ulf R. Borg, 44 Fox Run Way, Arnold, Md. 21012

[21] Appl. No.: 905,347

[22] Filed: Jun. 29, 1992

[51] Int. Cl.[5] .......................... A61M 15/00
[52] U.S. Cl. ................. 128/200.24; 128/205.12; 128/913; 128/DIG. 3
[58] Field of Search ............ 128/200.24, 202.16, 128/205.12, 913, DIG.; 26/104, DIG.; 28 422/44, 45, 48

[56] References Cited

U.S. PATENT DOCUMENTS

| | | | |
|---|---|---|---|
| 3,520,416 | 7/1970 | Keedwell | 261/104 |
| 3,692,648 | 9/1972 | Matloff et al. | 422/48 |
| 3,788,545 | 1/1974 | Budd et al. | 261/104 |
| 3,824,836 | 7/1974 | Lyshkow | 261/104 |
| 3,856,475 | 12/1974 | Marx | 422/48 |
| 3,894,954 | 7/1975 | Serur | 422/48 |
| 3,912,637 | 10/1975 | Esmond | 422/48 |
| 4,018,077 | 4/1977 | Leach | 261/104 |
| 4,061,484 | 10/1991 | Heldebrant | 424/78 |
| 4,187,390 | 2/1980 | Gore | 261/104 |
| 4,268,279 | 5/1981 | Shindo et al. | 55/16 |
| 4,443,480 | 4/1984 | Clark, Jr. | 424/352 |
| 4,576,590 | 3/1986 | Fiddian et al. | 122/45 |
| 4,661,092 | 4/1987 | Popovich et al. | 604/26 |
| 4,769,241 | 9/1988 | Heldebrant et al. | 514/832 |
| 4,781,889 | 11/1988 | Fukasawa et al. | 422/48 |
| 4,808,378 | 2/1989 | Nakanishi et al. | 261/DIG. 28 |
| 4,859,363 | 8/1989 | Davis et al. | 252/312 |
| 4,866,096 | 9/1989 | Schweighardt | 514/756 |
| 4,957,904 | 9/1990 | Falk et al. | 422/45 |
| 5,037,610 | 8/1991 | Fukasawa et al. | 422/48 |
| 5,106,579 | 4/1992 | Fukazawa et al. | 261/DIG. 28 |

FOREIGN PATENT DOCUMENTS 283850A 3/1988 European Pat. Off. .
1281273A 1/1987 U.S.S.R. .

Primary Examiner—Edgar S. Burr
Assistant Examiner—Aaron J. Lewis
Attorney, Agent, or Firm—Bell, Seltzer, Park & Gibson

[57] ABSTRACT

An extracorporeal lung assistance device having an oxygen-containing gas chamber positioned in such relationship to a gas exchange chamber that transfer of oxygen to blood and the withdrawal of carbon dioxide from blood disposed may be made. The gas exchange chamber has a blood flow channel extending through the gas exchanger defined by a microporous membrane forming a wall separating the blood flow channel from an oxygen, carbon dioxide exchange media. A second membrane supported in spaced-apart relationship from said first membrane. The space between the membranes is filled with the oxygen carbon dioxide exchange media.

14 Claims, 4 Drawing Sheets

EXTRACORPOREAL LUNG ASSISTANCE APPARATUS AND PROCESS

BACKGROUND OF THE

(1) Field of the Invention

This invention relates to an extracorporeal lung assistance device and process for using same. More particularly, this invention relates to a device whereby the carbon dioxide is removed and oxygen repleted in carbon-dioxide laden, oxygen-depleted blood.

(2) Description of the Prior Art

Respiratory failure requiring artificial support affects in excess of 300,000 people in the United States per year. Approximately one-half of these patients suffer from adult respiratory distress syndrome (ARDS). Adult respiratory distress syndrome is an acute inflammatory lung disease with a mortality rate of 50%. This disease is characterized by increased capillary permeability resulting from the development of interstitial edema and alveolar flooding.

For the vast majority of patients with ARDS, there is no specific treatment, only supportive therapy. Supportive therapy for ARDS focuses on mechanical ventilation. Mechanical ventilation, by creating a positive pressure gradient, results in the inflation of the lungs. This is a reversal of the normal lung which functions by utilizing negative pressure to ventilate the lung. Air movement into the lung results primarily in removal of carbon dioxide from the blood and secondarily in oxygenation of the blood. Current ventilatory support may be damaging to the lung. Pulmonary "Volutrauma" secondary to high ventilator tidal volumes and airway pressures may cause a capillary leak syndrome pathologically indistinguishable from ARDS. Thus, alternative life support modalities such as extracorporeal membrane oxygenation (ECMO) may be a therapeutic option for acute respiratory failure in both infants and adults.

Despite a 90% survival following the use of ECMO for infants and neonates, adult survival following ECMO remains approximately 50%. A recently developed technique involves a low frequency, positive pressure ventilation with extracorporeal CO2 removal (ECCO2R), employing veno venous extracorporeal circulation at relatively low blood flow rates. This method allows the lung to "rest" by applying only 3 to 4 breaths/minute at a limited peak airway pressure. Although physiologically attractive as a supportive technique, current ECCO2R techniques still have many of the same limitations as earlier ECMO techniques, including the need for systemic anticoagulants, i.e. the use of heparin, resulting in bleeding complication, high cost, and the requirement for additional specialized personnel, thereby limiting ECCO2R's clinical application.

Current membrane technology involves impervious membrane material but with micropores for gas transport. Micropores result in a direct blood to gas interface, which may cause serum protein denaturation, serum leakage and membrane failure. Alternative nonporous, gas pervious membranes alleviate the serum leakage problem but result in inefficient gas exchange. Inefficient membranes mandate large membrane surface areas and greater extracorporeal volumes, with greater likelihood of hemodynamic instability, blood trauma, bleeding complications.

U.S. Pat. No. 3,856,475 to Marx discloses a device for transferring oxygen into blood. Oxygen is dissolved into a fluorocarbon transfer medium. Oxygen-depleted blood passes through a multiplicity of small diameter, blood gas pervious silicon membrane transporting tubes. The oxygen is transferred through the walls of the tube to the blood using direct gas infusion to the gas exchange medium, resulting in inhomogeneous gas transfer medium secondary to bubble formation. Blood is propelled through the apparatus by compressing the gas exchange tubes.

In EPO-published Application No. 283,850, there is disclosed a method and device for pumping and oxygenating blood circulated extracorporeally in cardiovascular assistance. The European patent application No. 283,850 discloses recirculating gas exchange medium and functions as a heart/lung combination. The blood is propelled by alternating the pressure of gas exchange fluid. U.S. Pat. No. 3,894,954 is directed to a device for treating blood comprising a set of fluid channels for blood and a second set of channels for treatment fluid, each set being defined by a pair of panels of semipermeable membranes.

U.S. Pat. No. 4,781,889 discloses a hollow fiber membrane type artificial lung. Soviet Union Patent No. 1,281,273 discloses a method of extracorporeal oxygenation of blood involving pulse-type pumping by regular variation of pressure exercised by oxygenating blood fluid interface. Lastly, U.S. Pat. No. 4,661,092 discloses a peritoneal artificial lung which uses a perfluorocarbon oxygenating reservoir.

SUMMARY OF THE INVENTION

The general object of the present invention is to provide a device for the removal of carbon dioxide from blood and to replenish oxygen in oxygen-depleted blood.

A further object of this invention is to eliminate the blood-gas interface while utilizing highly efficient microporous membranes.

Another object of the invention is to provide an extracorporeal lung assistance device for use in the treatment of adult respiratory distress syndrome.

Yet another object of this invention is to provide a process for renewing oxygen depleted blood.

The above objects are achieved by the device of the present invention which is designed to replicate the anatomy of the human lung. The lung has an alveolar gas space, an alveolar membrane, an interstitial fluid/gel matrix, a vascular endothelial membrane and then blood. Carbon dioxide flows from the blood, through endothelial membrane, through fluid/gel matrix, through alveolar epithelium and into the alveolar space. The oxygen flow is in the opposite direction. The lung forms a three-compartment natural system: gas compartment (alveolus), interstitial medium and blood compartment (arterial, capillary and venous vessels). In effect, there are two membranes separating these three compartments. The natural interstitial fluid/gel matrix eliminates direct blood to gas interface. Additionally, the normal human lung has an alveolar surface area to capillary surface area ratio of approximately 1.14:1.00.

The device of the present invention provides a three-compartment system wherein blood is separated from the gas exchange liquid/gel by a microporous membrane, and the gas exchange liquid/gel is in turn separated from the gas by a second microporous membrane. The gas exchange liquid/gel medium in essence creates the equivalent of the normal human interstitial fluid/gel matrix. Additionally, the ratio of the surface area of the membrane separating the sweep gas compartment from the gas exchange media and the surface area of the membrane separating the gas exchange media from the blood compartment is much greater than 1, preferably at least 1.25:1.00. Forming the membrane separating the sweep gas compartment from the gas exchange media in the manner of a folded or accordion-like structure provides the increased sweep gas to gas exchange media interface. The increased ratio of surface areas is obtained in the three-compartment system where the membranes separating the compartments are independent structures. The three-compartment structure eliminates the blood/gas interface as well as the possibility of plasma water leakage into the gas phase. The microporous membranes may be of a suitable microporous membrane. The gas exchange media may be a perfluorocarbon.

An additional benefit from utilizing stationary gas exchange media separated from blood and gas using the device of this invention is that the risk of contamination of the gas exchange media is eliminated. The compartmented design provides for construction of a gas exchange apparatus with low resistance to blood flow, reducing blood trauma.

The present invention also provides a method for oxygenating blood by passing oxygen-depleted blood in contact with a first microporous membrane and simultaneously passing an oxygen-rich gas in contact with a second microporous membrane spaced apart from the first membrane by a perfluorocarbon. The oxygen passes through the second membrane, through the perfluorocarbon and then through the first membrane into the blood where the carbon dioxide is displaced from the blood through the membranes and exits the chamber.

Other objects, features and advantages of the invention will become evident from the foregoing detailed description of the invention taken in conjunction with the drawings, in which:

DETAILED DESCRIPTION OF THE PREFERRED EMBODIMENT

The present invention is directed to an extracorporeal lung assistance device having a three-compartment system wherein blood is separated from the gas exchange media by a selective microporous membrane and the gas exchange media is in turn separated from the sweep gas by a second microporous membrane. The three-compartment system represents the basic functional unit. The basic functional unit may be repeated in a parallel manner.

Figure 1:
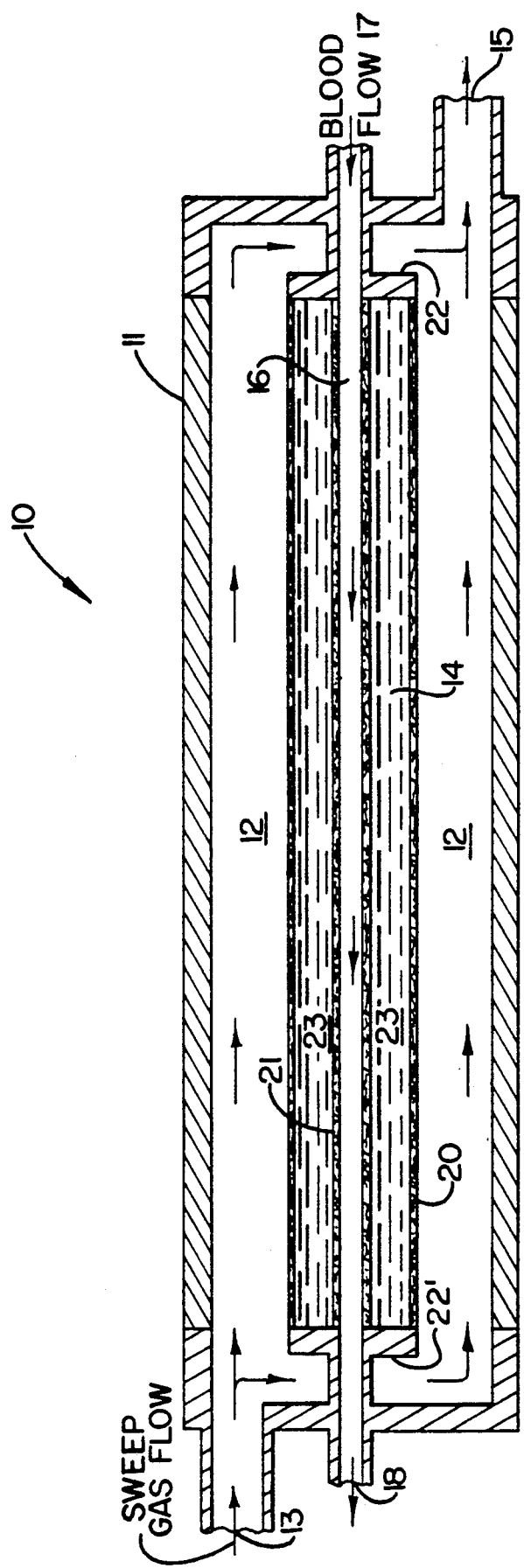
FIG. 1 is a cross-sectional elevation of the extracorporeal lung assistance apparatus of this invention.

Referring now to FIG. 1, there is shown an extracorporeal lung assistance device 10 constructed in accordance with the present invention which broadly comprises a housing 11 having an oxygen-containing gas chamber 12 therein. A blood flow channel 16 extends through the interior of the housing 11. Surrounding blood flow channel 16 is gas exchange member 14.

The oxygen gas chamber 12, surrounding gas exchange member 14 also disposed inside housing 11, has an oxygen-rich gas inlet 13, and an oxygen-poor gas outlet 15, at the other end of the housing from oxygen gas inlet 13. The oxygen-containing gas entering inlet 13 contains a significantly higher concentration of oxygen than when exiting. The amount of oxygen in the inlet gas stream is not critical so long as sufficient oxygen is present to replenish the blood. On the other hand, the exiting gas is higher in concentration of carbon dioxide than the entering gas as it sweeps the carbon dioxide through outlet 15. As used herein this gas stream is referred to as the "sweep gas".

The gas exchange chamber 14 comprises a blood flow channel 16 extending through the gas exchange chamber having an in-fluid communication through a blood inlet means 17 and a blood outlet means 18 connected through the exterior of housing 11 for communication to the circulatory system of a patient.

As shown in FIG. 1, gas exchange chamber 14 has an outer microporous membrane 20 defining a wall between the oxygen gas chamber and the gas exchange chamber. An inner microporous membrane 21 defining a wall between the gas exchange chamber 14 and the blood flow channel 16. The outer and inner membranes are supported in spaced-apart relationship by end support means 22, 22' at each end. While there is no definitive shape for the housing and the gas exchange member, it has been found in generally circular devices especially satisfactory. The space between the outer microporous membrane and the inner microporous membrane contains an oxygen and carbon dioxide transfer media 23. The housing and end supports may be made from any material suitable for medical applications, preferably a polycarbonate.

Figure 3:
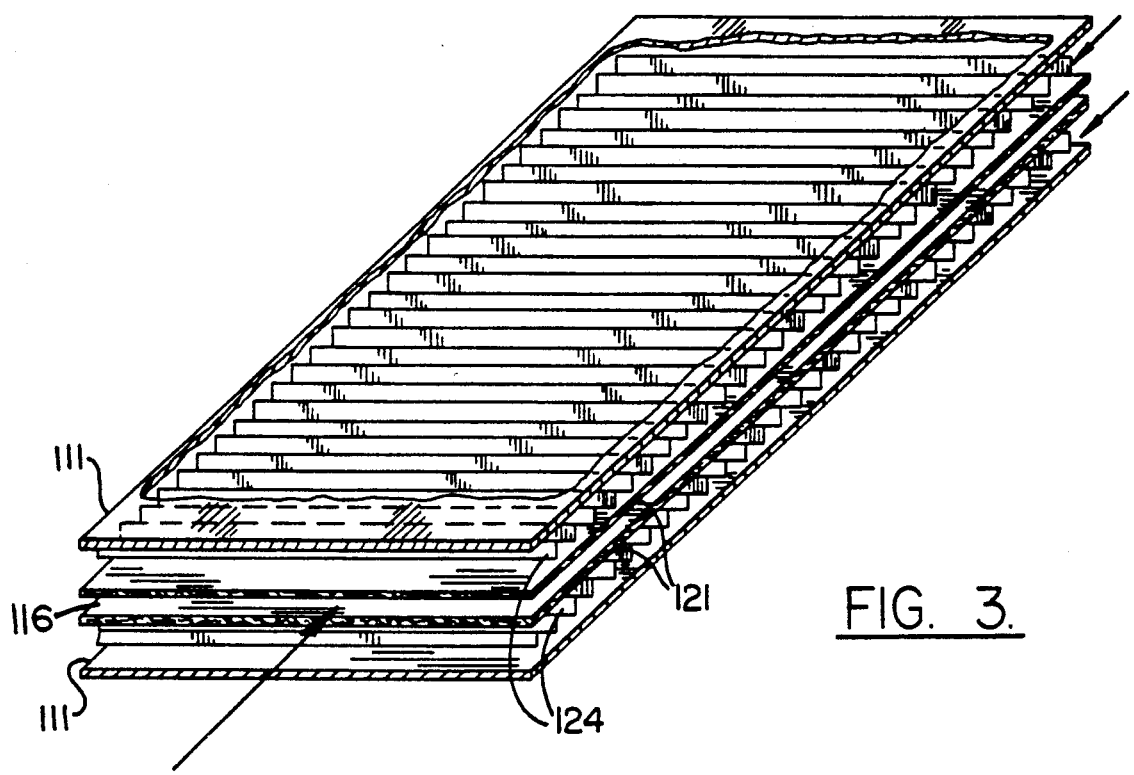
FIG. 3 shows a planar view of a gas exchange device of this invention where the gas transfer media interface to blood/transfer media interface ratio is greater than 1.25 to 1.00.

Although the device has been described as shown by the generally circular configuration of FIG. 3, it should be understood that other suitable shapes are contemplated for the device of this invention. One such embodiment is shown in the arrangement of FIG. 3 wherein oxygen-depleted blood flows through channel 116 formed between inner microporous membranes 121. Sweep gas is passed through the spaces formed between outer microporous membranes 124 and each side between plates 111. In actual use the elements shown in FIG. 3 are enclosed in a suitable housing of which plates 111 may form a portion thereof. As also shown in FIG. 3, the outer membranes 124 are folded accordion style as can be seen through the cut-out of plate ill, to increase the ratio of surface of outer membrane 124 to inner membrane 121. The space between the inner microporous membrane 121 and the outer microporous membrane 124 contains a gas exchange medium.

Figure 4:
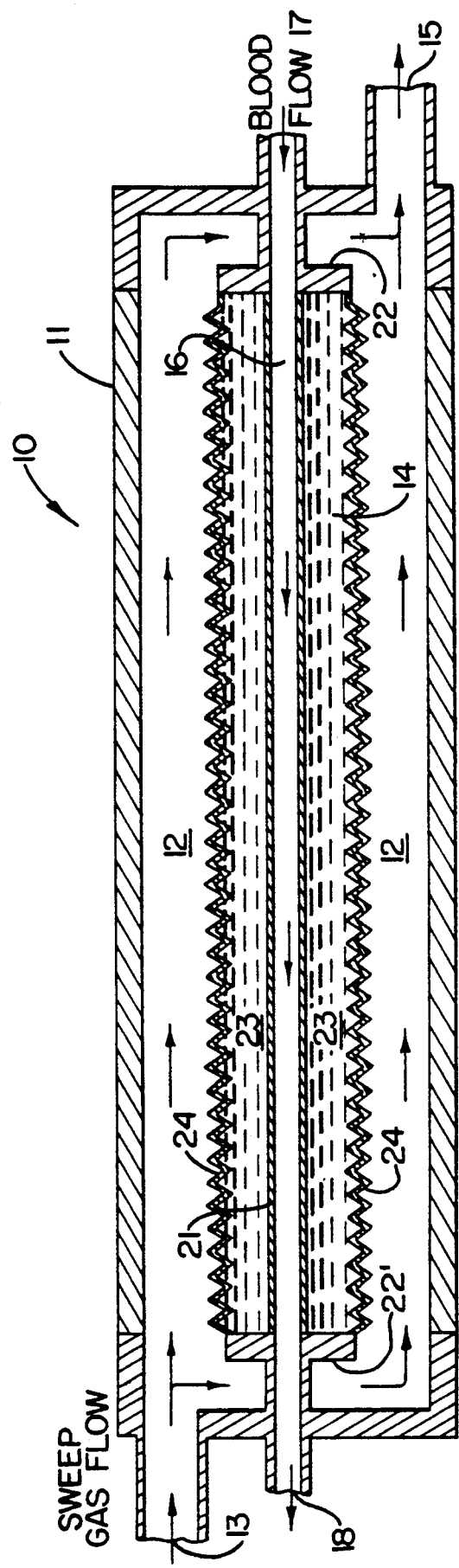
FIG. 4 shows a cross-sectional elevation of another embodiment of the extracorporeal lung assistance apparatus of this invention.

In a preferred embodiment, shown in FIG. 4, the ratio of the surface area of the membrane 24 and the surface area of membrane 21 is greater than 1 preferably greater than 1.25:1.00. The folding of outer membrane, 24 in FIG. 4 or 124 in FIG. 3, to increase the ratio of surface areas is most clearly shown in the embodiments of FIGS. 3 and 4 and is responsible for the increased oxygen rich gas (sweep gas) to gas exchange media interface. This can be accomplished by the compartmented structure where the microporous membranes separating the compartments are independent elements. The microporous membranes eliminate the blood/gas interface as well as the possibility of plasma water leakage into the gas phase. Appropriate valves and pumps may be employed to properly control flow through the device.

Both the inner microporous membrane and the outer microporous membrane used in the various embodiments of this invention are of suitable microporous materials. It has been found that an acrylonitrile and sodium methallyl sulfonate copolymer provides a particularly effective membrane. Such membranes are sold under the name AN69 ® by Hospal Ltd. of Basel, Switzerland. Other suitable membranes include microporous polypropylene, silicon, microporous polytetrafluoroethylene, polysulfone and polyamide membranes.

It has been found that perfluorocarbons are particularly suitable as the oxygen/carbon dioxide transfer media. The oxygen/carbon dioxide exchange media may be in the liquid, solid or gel state and should have a solubility for oxygen and carbon dioxide that is higher than blood and an affinity for the same gases that is less than blood. The term "perfluorocyclocarbon" as used herein means a cyclic compound of carbon, whereas the term "substituted derivatives thereof" characterizes substituted perfluorocyclocarbons with acyclic or alkyl side chains, preferably lower alkyl side chains. It should also be noted that the term "perfluoro-cyclocarbon" denotes substitution of all hydrogen atoms attached to the carbon atom chain or ring and any carbon side groups with fluorine. It is conceivable in the manufacture of such compounds that minor amounts of substantially fluorinated derivatives may be mixed with completely fluorinated compounds. This is permissible providing the lack of complete replacement of all hydrogens does not affect the essential characteristics of the liquid perfluorocarbons of this invention, particularly when the active hydrogens critically enhance the toxicity of the compounds when they are employed in oxygen transport agents in animals.

Included among the perfluoro-cyclocarbons which may be used in the device and process of this invention are perfluorobicy-clo[4.3.0]nonane, perfluorotrimethylcyclohexane, perfluoroisopropylcyclohexane, perfluoroendotetrahydrodicyclopentadiene, perfluorodamantane, perfluoroexo-tetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthene, perfluorotrimethylbicyclo(3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo-[4.3.0.]nonane, perfluoro-p-diisopropylcyclohexane, and perfluoro-m-diisopropylcyclohexane.

It is also to be understood that the fluorocarbons that are useful according to the principles of this invention may be generally termed "perfluoro-cyclocarbons" or "perfluoro-carbocyclic compounds" or "cyclic perfluorocarbons". The term used predominantly in this description is perfluorocyclocarbon, however, the term cyclic perfluorocarbons or perfluorocarbocyclic compound are considered alternative expressions. The term "carbocyclic" or "cyclocarbon" means a homo-cyclic compound of carbon, e.e., a ring or rings of carbon atoms. The carbocyclic compound may be monocyclic as in the case of cyclohexane or bicyclic as in the case of naphthalene or polycyclic as in the case of phenanthrene. Furthermore, other polycyclic perfluoro compounds whose ring structure cannot be aromatized without destruction of its original carbon-to-carbon cyclic bonds are included. Thus, the later mentioned perfluorocompounds which may be employed in this invention are distinguished from the perfluorodecalin compounds mentioned above, or other similar compounds which can be aromatized. The carbon ring can be alkylated with a lower alkyl group or groups such as methyl or ethyl as in the case of perfluoro(methylcyclohexane) or perfluoro(decahydrodimethylnaphthalene). Perfluorocyclocarbons of this invention may be formed of "neat" perfluorocarbon liquids or solids and often, due to their mode of manufacture, are mixtures of perfluorocyclocarbons.

Figure 2:
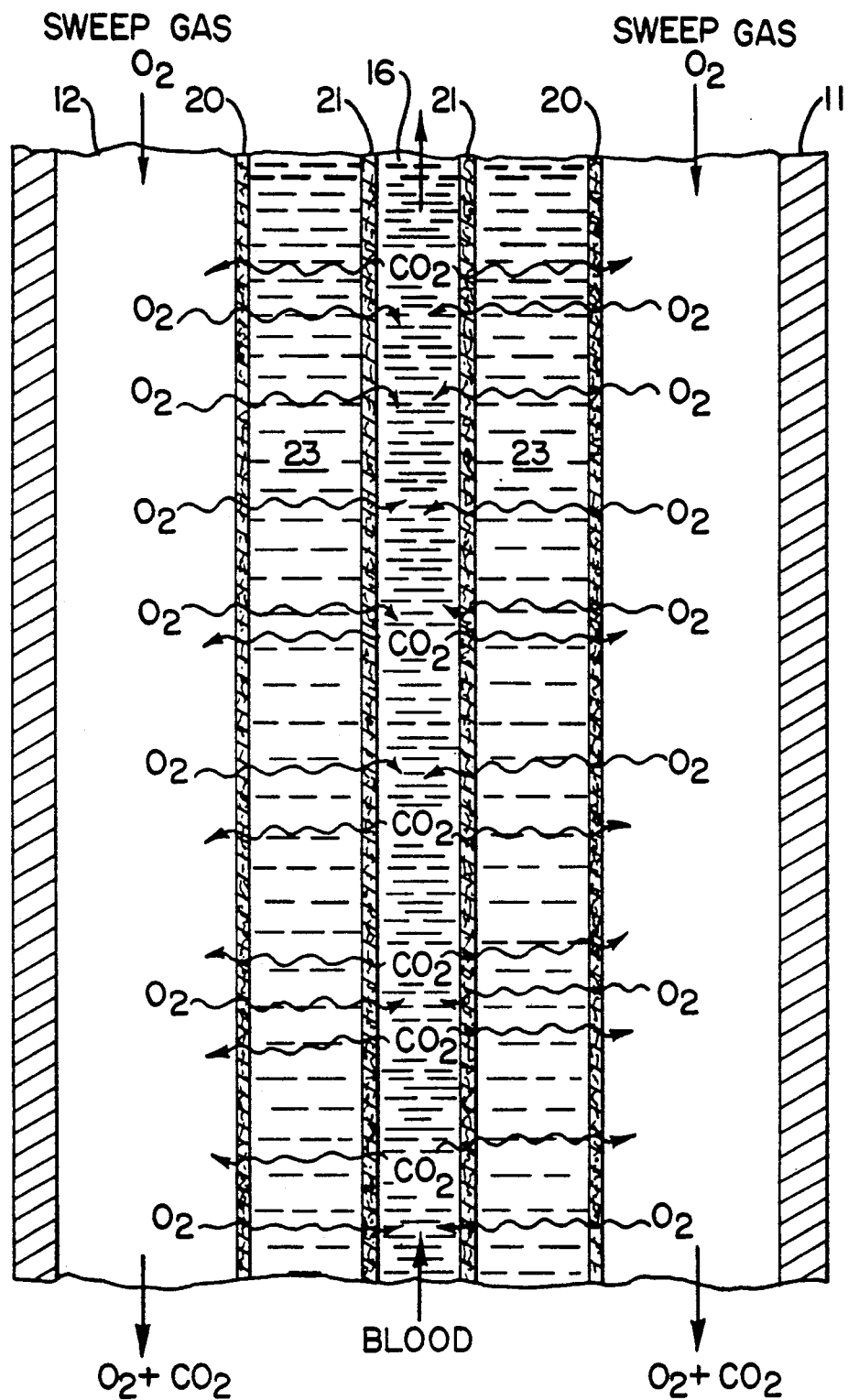
FIG. 2 is a cross-sectional view showing the oxygen/carbon dioxide gas interchange interface using the apparatus and process of this invention.

In operation the device, in effect, acts as a two stage oxygen/carbon dioxide exchanger with the inner membrane acting as one stage and the transfer media serving as a second stage. In practice, oxygen-poor blood is passed from a patient and as shown in FIG. 11 the blood which is low in oxygen content passes into the blood channel and as it passes through inlet 17 into the blood channel 16. At the same time sweep gas is introduced through inlet 13 and passes in a counter current direction with the blood. The sweep gas enters the device at a flow rate between 1 and 20 liters per minute and following exchange with carbon dioxide exits outlet 15. The exchange of oxygen and carbon dioxide is illustrated in FIG. 2 which shows the oxygen-poor blood entering blood flow channel 16 and oxygen-rich sweep gas entering chamber 12 at the opposite end. Simultaneously with the oxygen exchange, carbon dioxide is removed from the blood, transferred through membrane 21 through transfer media 23, and through outer membrane 20 into gas chamber 12 where it mixes with the left over sweep gas and is passed from housing 11 to a gas collector. A planar view of a preferred embodiment is shown in FIG. 3.

The size of the device will be determined by adjusting the various parameters to obtain a suitable carbon dioxide exchange and will vary depending upon such parameters as blood flow rate and, in particular, the ratio of the outer membrane interface to the inner membrane interface. The larger the ratio of these interfaces, the more rapid the transfer of oxygen and carbon dioxide will occur. The exchange of carbon dioxide and oxygen generally takes place in a sufficiently short time that the blood recirculated to the patient is normally of or close to body temperature.

EXAMPLE 1

An extracorporeal lung assistance device having an inner surface area membrane of 1 square meter and an outer membrane having a surface of 1.5 square meters was made from an acrylonitrile sodium methallyl sulfonate copolymer (AN69 from Hospal, Ltd.). The gas exchange media was FC72 perfluorocarbon. Carbon dioxide laden blood ($CO_2$ content 56 vol%) was passed at a flow rate of 500 ml/min through the device. A gas containing 100% pure oxygen was passed the other direction at 4000 ml/min. The blood leaving the device had 44 vol% carbon dioxide content, resulting in a carbon dioxide clearance of 60 ml/min/m². With a ratio of 1:1, the carbon dioxide content in the same device was 50 vol%, corresponding to carbon dioxide clearance of 30 ml/m².

These results show that an interface ratio greater than 1 is a more efficient gas exchange apparatus that closely resembles the human lung. The biocompatability of the microporous membrane and exchange media reduces the blood damage, thus reducing the need for anticoagulant use during extracorporeal life support. The device of this invention has the advantages of greater efficiency than currently used solid membrane lungs used for ECMO/ECCO2R, resulting in less extracorporeal blood, the elimination of gas/blood interfaces and use as a technique similar to proven and well established methods for continuous arterio-veno hemodialysis, and less cost and labor intensive than traditional extracorporeal techniques.

Although illustrating embodiments of this invention have been described in detail hereinabove with reference to the accompanying drawings, it is to be understood that the invention is not limited to those precise embodiments, and that various changes and modifications may be readily affected by persons of ordinary skill without department from the spirit or scope of the invention as being set forth in the following claims.

WHAT IS CLAIMED IS

1. An extracorporeal lung assistance device comprising:
  a housing having at least one oxygen-containing gas chamber, and a gas exchange member adjacent said oxygen-containing gas chamber;
  said oxygen-containing gas chamber having an oxygen-rich gas inlet and an oxygen-poor gas outlet;
  said gas exchange member comprising a blood flow channel extending through said gas exchange member having blood inlet and blood outlet means in fluid communication with the exterior of said housing for communication to a circulatory system,
  said gas exchange member having an outer microporous membrane defining a wall between the oxygen containing gas chamber and the gas exchange member, an inner microporous membrane defining a wall between the gas exchange member and the blood flow channel, said membranes being supported in spaced apart relationship by end support means, and the space between said outer microporous membrane and said inner microporous membrane containing an oxygen and carbon dioxide transfer media whereby the carbon dioxide in the oxygen-poor blood is exchanged for oxygen as the oxygen-blood passes through the gas exchange member.

2. The extracorporeal lung assistance device according to claim 1 including means connecting the oxygen-rich inlet to an oxygen-rich supply and the oxygen poor outlet to a gas collection means.

3. The extracorporeal lung assistance device according to claim 1 including mean connecting the blood inlet and outlet to the circulatory system of a patient.

4. The extracorporeal lung assistance device according to claim 1 wherein at least one of said membranes is an acrylonitrile and sodium methallyl sulfonate copolymer.

5. The extracorporeal lung assistance device according to claim 1 wherein at least one of said membranes is selected from the group consisting of microporous polypropylene, silicone, microporous polytetrafluoroethylene, polysulfone, and polyamide membranes.

6. The extracorporeal lung assistance device according to claim 1 wherein said oxygen and carbon dioxide transfer media is a perfluorocarbon.

7. The extracorporeal lung assistance device according to claim 1 wherein the ratio of the surface area of the membrane defining the wall between the oxygen containing gas chamber and the gas exchange member to the surface area of the other membrane is greater than 1.

8. The extracorporeal lung assistance device according to claim 6 wherein the ratio of the surface area of the membrane defining the wall between the oxygen containing gas chamber and the gas exchange member to the surface area of the other membrane is from about 1.25:1.00 to about 3.0:1.0.

9. The extracorporeal lung assistance device according to claim 1 wherein said housing is a generally circular configuration and said gas exchange member is disposed within said housing in such manner that said oxygen-containing gas chamber surrounds said gas exchange member in spaced-apart relationship.

10. The extracorporeal lung assistance device according to claim 1 wherein said housing is a generally flat configuration and said gas exchange member is generally flat in configuration and disposed within said housing in such a manner that said oxygen containing gas chamber is adjacent to said gas exchange member on at least two sides in spaced-apart relationship.

11. A method for treating blood comprising:
  (a) providing a source of oxygen containing gas;
  (b) providing a housing having at least one oxygen containing gas chamber and a gas exchange member including a first microporous membrane adjacent said gas chamber;
  (c) providing a blood flow channel having a blood inlet and a blood outlet extending through said gas exchange member;
  (d) providing a second microporous membrane as a wall between said gas exchange chamber and said first microporous membrane in spaced relationship to the first microporous membrane while supporting said microporous membrane using end support means;
  (e) providing an oxygen and carbon dioxide transfer media between said microporous membranes;
  (f) passing said oxygen containing gas in contact with said first microporous membrane and simultaneously passing oxygen-poor blood in contact with said second microporous membrane, whereby carbon dioxide within the oxygen-poor blood is exchanged for oxygen across said microporous membranes and said transfer media.

12. The method for treating blood according to claim 11 wherein at least one of said membranes is an acrylonitrile and sodium methallyl sulfonate copolymer.

13. The method of treating blood according to claim 11 wherein at least one of said membranes is selected from the group consisting of microporous polypropylene, silicone, microporous polytetrafluoroethylene, polysulfone, and polyamide membranes.

14. The method for treating blood according to claim 11 wherein said oxygen and carbon dioxide transfer media is a perfluorocarbon.

* * * * *

UNITED STATES PATENT AND TRADEMARK OFFICE
CERTIFICATE OF CORRECTION

PATENT NO. : 5,277,176
DATED : January 11, 1994
INVENTOR(S) : Nader M. Habashi et al.

It is certified that error appears in the above-indentified patent and that said Letters Patent is hereby corrected as shown below:

Column 1, line 5, after "THE" insert --INVENTION--.

Column 4, line 56, delete "ill" and substitute --111-- therefor.

Column 5, line 55, delete "clo(3.3.1.]nomane and substitute --clo[3.3.1]nomane-- therefor.

Column 6, line 26, delete "11" and substitute --1-- therefor.

Column 7, line 52, delete "oxygen-blood" and substitute --oxygen-poor blood-- therefor.

Column 8, line 4, delete "I" and substitute --1-- therefor.

Column 8, line 45, delete "membrane" and substitute --membranes-- therefor.

Signed and Sealed this

Second Day of August, 1994

Attest:

BRUCE LEHMAN

Attesting Officer  Commissioner of Patents and Trademarks